United States Patent [19]
Apfel

[11] Patent Number: 5,840,276
[45] Date of Patent: Nov. 24, 1998

[54] ACTIVATABLE INFUSABLE DISPERSIONS CONTAINING DROPS OF A SUPERHEATED LIQUID FOR METHODS OF THERAPY AND DIAGNOSIS

[75] Inventor: Robert E. Apfel, New Haven, Conn.

[73] Assignee: Apfel Enterprises, Inc., New Haven, Conn.

[21] Appl. No.: 780,337

[22] Filed: Jan. 8, 1997

Related U.S. Application Data

[60] Provisional application No. 60/009,699, Jan. 11, 1996.
[51] Int. Cl.⁶ .............................. A61K 49/04; C09K 3/00
[52] U.S. Cl. .......................... 424/9.52; 424/455; 424/9.3; 424/9.4; 514/937; 252/314; 252/350
[58] Field of Search ..................... 424/9.52, 9.5, 424/455, 9.3, 9.4; 548/422, 418, 407; 514/410, 937; 264/4.1; 427/213.3; 252/312, 314, 350; 600/458

[56] References Cited

U.S. PATENT DOCUMENTS

| | | |
|---|---|---|
| 4,143,274 | 3/1979 | Apfel . |
| 4,350,607 | 9/1982 | Apfel . |
| 4,613,758 | 9/1986 | Ing et al. . |
| 5,209,720 | 5/1993 | Unger . |
| 5,393,524 | 2/1995 | Quay . |
| 5,403,575 | 4/1995 | Kaufman et al. ....................... 424/1.89 |
| 5,439,669 | 8/1995 | Kaufman et al. . |
| 5,536,489 | 7/1996 | Lohrmann et al. . |
| 5,542,935 | 8/1996 | Unger et al. ............................ 604/190 |
| 5,558,854 | 9/1996 | Quay . |
| 5,573,751 | 11/1996 | Quay ..................................... 424/9.52 |

*Primary Examiner*—Gary E. Hollinden
*Assistant Examiner*—Michael G. Hartley
*Attorney, Agent, or Firm*—Fish & Richardson P.C.

[57] ABSTRACT

Dispersions of superheated drops of immiscible liquids in aqueous continuous phase suitable for infusion into a human or other animal, the drops being vaporizable in a selected body location by ionizing radiation or ultrasound. The dispersions can be used to form diagnostic contrast agents, to improve diffusion of drugs, to occlude capillaries and to deliver drugs selectively in a localized body region.

31 Claims, No Drawings

ACTIVATABLE INFUSABLE DISPERSIONS CONTAINING DROPS OF A SUPERHEATED LIQUID FOR METHODS OF THERAPY AND DIAGNOSIS

This application claims the benefit of U.S. Provisional application Ser. No. 60/009,699, filed Jan. 11, 1996.

This invention relates to delivery of diagnostic and therapeutic agents in humans and animals.

BACKGROUND

Selective delivery of drugs to a particular target location in the body of a human or other animal has recognized benefits. Cancer chemotherapy is the best-known example. Cancer chemotherapy (the treatment of cancer with cytotoxic drugs) has produced dramatic improvements in the treatment of patients with hematopoietic and lymphoid malignancies; for example, childhood leukemia and Hodgkin's disease are now highly curable diseases. Antineoplastic drugs are also effective in treating microscopic metatases, when given in combination with localized treatment (surgery and/or radiotherapy) to control the sites of bulk disease. Cancer chemotherapy has proven less effective in the treatment of large solid malignancies. Solid tumors (e.g., cancers of the lung, breast, prostate, cervix, brain, head and neck) are the most common cancers of adults, and account for the vast majority of cancer deaths in the United States today. Almost without exception, anticancer drugs are toxic to cells of critical normal tissues, as well as to cancer cells. The intensity of treatment with these drugs is limited by the ability of normal tissues (and the patient) to tolerate the therapy, rather than by the amount of drug needed for optimal treatment of the tumor. Perhaps the greatest barrier to the effective treatment of solid tumors with antineoplastic drugs is the problem of drug delivery. R. K. Jain, "Delivery of novel therapeutic agents in tumors: physiological barriers and strategies," Journal of the National Cancer Institute (NIH), 81, 570–576(1989).

Selective delivery of anticancer drugs to a needed location, for example, the site of a solid tumor, is recognized to have potential value. A number of approaches have been tried in laboratory and clinical studies to improve the treatment of solid cancers. Direct topical application of drugs and intratumoral injection of drugs has had limited success, largely because the diffusion of drug from the administration site is inadequate. Selective infusion of tumors through a major artery supplying the tumor has been effective only in some settings. Solid "slow release polymers" containing antineoplastic drugs have been implanted into tumors. These attempts to deliver drugs directly to tumors have yielded limited success in some contexts, but have not proven to be widely applicable or effective. R. Langer, "New methods of drug delivery," Science, 249, 1527–1533(1990).

Different approaches have been tried for the purpose of "targeting" intravenously injected drugs. Ibid. Drugs have been attached to antibodies directed against specific tumor antigens. Drugs have been encapsulated in liposomes, starch microspheres, or other encapsulation vehicles in the hopes that this would protect the drug from inactivation in the blood and that these particles would lodge selectively in the abnormally tortuous tumor blood vessels. Attempts have been made to target liposomes, for example by developing magnetic liposomes and applying magnets to the surface of the tumor or by administering heat-sensitive liposomes and delivering heat in order to cause a tumor to become hyperthermic. Limited success has been observed. Drug release in non-target tissues remains a limitation.

In diagnostic technology, ultrasound imaging is known. It is known that small gas bubbles can be employed as ultrasound contrast agents and that a liquid which is immiscible in blood and which boils slightly below body temperature (for humans, 37° C.) can create such small bubbles in the body. Bubbles may be too large to enter the capillaries of a tumor, for example, which is an imaging limitation.

An aspect of this invention is intravenous dispersions for selective intravenous delivery of therapeutic and diagnostic agents to a particular location in the body, comprising drops of a liquid that is superheated, most preferably highly superheated, at the temperature and pressure of use and that can be triggered to vaporize at a particular location by radiation or ultrasound. Triggering activates the dispersions for a localized purpose. Bubbles formed from vaporized drops may serve as therapeutic or diagnostic agents. Alternatively or in addition, the drops may carry a drug, which is released at a particular location in the body by such vaporization.

An aspect of this invention is intravenous drug delivery dispersions comprising superheated, drug-carrying drops from which a drug can be released in a selected "target" location in a living body by application of a localized or localizable energy source, namely radiation or ultrasound, to activate the dispersions.

Another aspect of this invention is methods of using intravenous dispersions of superheated drops for therapy or diagnosis at a selected target location in the body of a human or other animal which includes administering the dispersions intravenously and subjecting the selected target location with a localized or localizable source of radiation, most preferably x-ray or gamma ray, or ultrasound capable of nucleating the superheated drops to transform them into the vapor phase. The transformation activates the dispersion for a therapeutic or diagnostic purpose, such as to serve as a contrast agent or to deliver a drug.

SUMMARY OF THE INVENTION

This invention includes dispersions comprising drops of a superheated liquid dispersed in an injectable host fluid such as intravenous fluid. The dispersions are infusable, that is, suitable for infusion into the body of a human or other animal. The drops are "practically immiscible" in body fluids (for example, blood or urine) and host fluids with which they will be in contact. By this is meant the drops have sufficient immiscibility with body fluid of patients, whether human or other animals, to retain their integrity as drops after administration to permit localized vaporization and sufficient immiscibility with any intravenous or other host fluid used for infusion of the drops to retain their integrity as drops during preparation, storage, if any, and administration. Generally, solubility in aqueous host and body fluids should not exceed a few percent during the pertinent time period.

The drops are a liquid having a boiling temperature below body temperature at atmospheric pressure. Preferred components for such drops are organic compounds such as fluorocarbons, chlorofluorocarbons and hydrocarbons. In some embodiments, inorganic components, such as silicone oils, can be used. Mixtures of components or additives such as salts can be used to adjust the boiling point of the drop material in known fashion. Additional liquid components can be included, for example to dissolve a drug. For ease of handling, preferred dispersions are emulsions. Emulsions according to this invention also include an emulsifier, a component that protects the drops by coating them and preventing their coalescing.

The drop composition has a degree or amount of superheat rendering the drops susceptible to vaporization by a type and amount of radiation or ultrasound tolerable by the body. The lower the boiling point, the greater the amount of superheat of the drops. The greater the degree of superheat, the more susceptible the drops are to nucleation. Preferably, the drop material is sufficiently superheated that the drops will readily boil, or vaporize, when hit with radiation from a convenient source, or with ultrasound, which initiates boiling or "nucleates" the drops. The preferred degree of superheat is more than 17 degrees in Celsius units, or 17 Celsius degrees, for this purpose. Most preferably the degree of superheat is very high for nucleation by common medical radiation sources such as x-rays or gamma rays, in the range of about 60–80 Celsius degrees, near but at least a few degrees below the amount of superheat that causes homogeneous nucleation, which occurs typically for pure organic liquids at approximately 0.9 Tc, where Tc is the critical temperature of the liquid in degrees K. The homogenous nucleation temperature for a given dispersion can be determined by gradually warming the dispersion until all the drops vaporize, which occurs at the homogenous nucleation temperature. For use at human body temperature, 37° C., and pressure (slightly above or below one atmosphere), this means the drops preferably have a boiling point below 20° C., more preferably below −5° C., and most preferably below −15° C. For most liquids a boiling point within the range of −15° C. to −30° C. at atmospheric pressure will be found to be suitable for nucleation in humans by x-rays. By "radiation" I mean ionizing radiation (such as x-rays, alpha, beta, gamma and neutron), particles or waves capable of causing an electron to be removed from an atom or molecule. "Ultrasound" used herein means acoustic waves that can produce physical effects, including nucleation of superheated drops into bubbles and the vibration of those bubbles. Generally ultrasound is above audible frequencies, that is, above 20 KHz (20,000 Hertz). Ultrasound for diagnostics is generally 1–20 MHz (megahertz). Ultrasound for therapeutic applications is generally 20 KHz to 5 MHz.

The bubbles formed by vaporization of the superheated drops may serve as therapeutic or diagnostic agents. They may occlude blood flow in capillaries of a tumor, for example. They may deliver oxygen. Drops may vaporize in a selected location to form bubbles that serve as contrast agents for diagnostic imaging, including x-ray, ultrasound and MRI. Some capillary regions may be entered by drops where larger bubbles, if preformed, would not enter. Bubbles may be stimulated with ultrasound to impart motion to the bubbles, thereby aiding in dispersal of a drug that has been delivered to the selected body location by means of a dispersion according to this invention or in some other manner. In certain embodiments, a drug is added to the superheated liquid, which may be said to be a "carrier" and to be "doped" with the drug. I use the term "drug" in the very broadest sense to include a substance intended for use in the diagnosis, cure, mitigation, treatment or prevention of disease, or a substance other than food intended to affect the structure or function of the body. I refer to "drug" in the singular, but it will be understood that combinations of drugs are to be included as well.

Dispersions according to this invention are prepared by dispersing a superheatable liquid drop composition in an aqueous liquid under pressure. The aqueous liquid may be the infusable host or an aqueous liquid intended to be replaced by the ultimate host liquid. Depending on the size of the drops formed and their density relative to the aqueous phase, the dispersion may or may not be mechanically stable. Drops may tend to settle rather rapidly in some embodiments. Coalescing of drops is avoided by making the drops sufficiently small (generally less than 1 μm average diameter) that Brownian motion maintains the dispersion, by application of gentle agitation to maintain the dispersion, by addition of a gelling agent or thickening agent to prevent or at least sufficiently retard settling, by addition of an emulsifier to coat the drops and prevent their coalescing when they settle, or by some combination of those techniques. By addition of a gelling or thickening agent, dispersions have been maintained without agitation for a period of three months with no indication of significant settling. A preferred dispersion technique is to mix a drop composition and a host solution or replaceable aqueous phase under pressure, and then to shake or sonicate the mixture to disperse the drop material. The final dispersion includes an aqueous infusion medium, typically an intravenous saline solution.

Infusion into the body is by conventional means. Infusion can be, for example, by means of a catheter inserted into a selected body location, by injection directly into a tumor or organ, or by intravenous drip. It is noted that injection into the bloodstream closely upstream to the body part of interest, sometimes referred to as the "target" or "target location," aids in delivering a high concentration of superheated drops as compared to more remote injection.

As the superheated drops are subjected to ionizing radiation or ultrasound, they vaporize (boil), thereby forming bubbles and releasing any drug with which they are doped into the local environment. I refer to this as activation of the dispersion. Vaporization is localized by localizing the body portion subjected to radiation or ultrasound. External radiation sources and ultrasound are localizable in that they may be directed to selected, specific locations in the body. Implanted radiation sources ("brachytherapy") may also be used for localized effect. As superheated drops pass through the target location, a radiotherapy source (either external or brachytherapy) or ultrasound is applied to cause the superheated drops to boil, thereby forming bubbles and freeing a drug, if present, at the selected local site, for example, a tumor. If infusion is by intravenous injection, dispersed superheated drops will be recirculated naturally through the selected location. At each pass through the site of localized energy application (radiation or ultrasound), additional bubbles are formed and, if present, additional drug is released. Such localization of bubbles and drugs has benefit in cancer chemotherapy and in radiation/drug combination or combined modality therapy (especially of hard-to-treat solid tumors). Higher doses of a cancer drug can be delivered in this way than otherwise can be tolerated by the body, because most of the body does not receive the full dose that is delivered locally.

DETAILED DISCUSSION

Drop material is a liquid composition that is superheated at body temperature and pressure, as has been stated. One composition that has been evaluated includes two parts of chloro-pentafluoroethane ($C_2ClF_5$), one part pentane, and one part acetone into which the drug mitomycin C had been dissolved. All three ingredients are miscible. Pentane modifies both the boiling point and the density of the drop material.

The proportions of materials helps to determine the composition's mechanical stability and also the degree of superheat. The greater the degree of superheat, the less energy required to initiate the transformation of the drops from the metastable liquid state to the vapor state. In other words, more greatly superheated drops are more easily nucleated. For many superheated liquids, if the degree of superheat is sufficiently great (more than about 50 Celsius degrees above its boiling temperature at the temperature of use), then the drops of the tested composition will be triggered at body temperature by a simple x-ray or gamma ray source, commonly available in hospitals. For less superheat, a neutron source or perhaps even a proton source is needed to trigger the drops at body temperature. The use of x-rays has obvious advantages for practical applications. Therefore, the composition selected for testing was made to be sensitive to x-rays and gamma rays at body temperature (37° C.).

Drop material is dispersed in an aqueous liquid, which can be the infusable host liquid but need not be. Dispersion can be in a first aqueous liquid, which is then substantially replaced by another aqueous liquid to form the dispersion to be infused. A concentrate can be prepared for dilution to the desired concentration in host solution. In preferred embodiments dispersion is accomplished in the presence of an emulsifier, so that the dispersion is an emulsion. Emulsified drops can be concentrated by settling or gentle centrifugation followed by decantation of most of the original aqueous phase. This emulsifier coats the drops and prevents them from coalescing at this concentrated stage. The final infusable composition can then be made by addition of a new aqueous phase, preferably one containing a gelling or thickening agent to prevent settling, and mixing, for example, stirring. If the dispersion is not an emulsion, settling may cause the drops to coalesce. This can be prevented, where necessary, by physically maintaining the dispersion, as by gentle agitation, until the time of infusion. Dispersion is performed under pressure and, preferably, at a temperature below room temperature. After the dispersion is prepared, pressure is relieved. At this point the drops have a significant degree of superheat but they do not vaporize. The amount of superheat of the drop material is below the homogenous nucleation temperature, which is approximately 0.9 times the critical temperature (in degrees K.) for most organic liquids and approximately 83 Celsius degrees of superheat. Consequently, the boiling point of the drop material is adjusted to be above −30° C. at atmospheric pressure. Also nucleation is avoided prior to use. Preparing the dispersion under pressure aids in avoiding premature vaporization.

Some of the techniques useful for preparing and administering the system according to this invention are those known for drug carrying liposomes or perfluorochemical emulsions. However, drop formation is always done under pressure.

Methods for how to make the superheated drop dispersion include, but are not limited to:

1) A drug, if used, can be either soluble or insoluble in the superheated drop liquid composition. In the former case, it is dissolved under pressure, in the superheated drop liquid or, if necessary or desired, dissolved in one component of the drop material prior to constituting the final drop material. In the latter case, it must be in a fine powder form. Fineness can be increased as necessary to ensure that the drug is evenly dispersed among the superheated drops. Standard grinding techniques and/or pulverizing techniques are among several well established procedures for making solid materials into powder form.

2) Liquid drop material is dispersed (oil-in-water dispersion) into an aqueous intravenous fluid or other aqueous "host" solution. Dispersion occurs at pressures equaling or exceeding the vapor pressure of the drop material at the particular temperature of the mixing so that it remains a liquid and does not vaporize during this processing. Dispersion can take place by many standard techniques, such as rapid stirring of the drop material into the host liquid, high intensity ultrasonic waves, and other methods generally known. Alternatively, a stream of the drop liquid is introduced into a stream of the intravenous fluid so that the stream breaks up into drops due to a Rayleigh-Taylor instability as well as the shear forces exerted by the outer stream of intravenous fluid.

The drops have an average diameter in the range of 0.05–20 $\mu$m, preferably in the range of 0.05–10 $\mu$m and more preferably in the range of 0.1–5 $\mu$m. Drop size varies with the manner of dispersion. Stirring or shaking by hand can be used to produce larger drops, for example, 10 $\mu$m and above. Sonication with an ultrasonic cleaner can be used to produce smaller drops, in the range of 1–10 $\mu$m. For even smaller drops an ultrasonic horn emulsifier can be used. In all instances dispersion is performed under pressure. As a rough indicator, bubbles can be expected to have an average diameter six to nine times larger than the drops. If the drops have an average diameter below about 1 $\mu$m, they may remain suspended owing to Brownian motion. A stable dispersion can be obtained, for example, by using an ultrasonic horn emulsifier to produce very small dispersed drops having an average diameter of, for example, in the range 0.05 to 0.5 $\mu$m, allowing any large drops to settle and decanting the major fraction containing small, non-settling drops. Otherwise, unless the drops are coated with an emulsifier to prevent them from coalescing, coalescence must be prevented. Addition of a gelling or thickening agent may suffice, as may gentle agitation, or a combination of the two techniques.

Superheated drop dispersions according to this invention are physically stable from premature vaporization caused by shear stresses in handling and infusion. This flow stability was demonstrated by mixing 3 ml of a dispersion with 50 ml of water in a 60 ml glass syringe. The mixture contained roughly $10^7$ drops per ml. The mixture was flowed through a 1.5 mm glass tube (inside diameter) by a syringe pump. The tube was 20 cm in length and was maintained at 37° C. by a thermobath. At flow rates of 0.5 ml/min (0.45 cm/sec average), 1 ml/min (0.9 cm/sec average) and 2 ml/min (1.8 cm/sec average), no bubble formation was observed using a low power microscope. Similar results were obtained using plastic tubing.

The drop material often does not form a stable dispersion in a saline solution. The drops either settle or can be made to do so by gentle centrifuging. This is not a problem and can be utilized to advantage if the dispersion is an emulsion, because concentrated drops remain separate due to the encapsulating material. They are nonetheless handled carefully to avoid premature vaporization, which at this stage can become a chain reaction.

When an emulsion is used, the drop material can be added to the intravenous host fluid in the concentration to be infused. Gentle agitation at the time of use can, if needed, redistribute settled drops. If long-term stability of the emulsion in the intravenous fluid is not great, addition may closely precede administration. Because the drops separate, either naturally or with centrifugation, they can be collected by decanting most of the original host liquid and then, at a later time, diluted with the requisite amount of the particular infusion liquid to be used for a given application.

A more stable emulsion or a stable concentrate can be prepared. Most of the original host liquid can be removed, as by simple decantation. It can be replaced by host solution containing a gelling or thickening agent, e.g., a colloid or polymer which prevents settling. The gelling or thickening agent preferably should not be toxic in the amount used, which should not be so much as to make administration practically difficult.

3) Following infusion of the dispersion, the drops are nucleated locally, sometimes referred to as "triggering the drops" by radiation or ultrasound. The energy source can take several forms, including, but not limited to:

A) An x-ray machine, such as used in diagnostic x-rays, is a directable, and hence, localizable source of radiation external to the body;

B) Radiological sources, for example, cobalt 60, producing gamma x-rays, are also directable sources of external radiation;

C) Any number of imbedded radiation sources (called brachytherapy sources) are localized sources of radiation internal to the body;

D) A medical accelerator source of radiation (either x-rays or high energy electrons) is also a directable source of external radiation that will penetrate into tissue to trigger drops into bubbles; and E) An ultrasound source, such as used for diagnostic ultrasound examinations, or more powerful sources of ultrasound used in therapeutic applications of ultrasound (for example, to create hyperthermia) can be directed to the desired site (either coupled to the skin via a coupling gel or by a water standoff), triggering drops to form bubbles.

An advantage of the dispersion of this invention is that the superheated drops are vaporized by a convenient source of radiation or ultrasound while circulating through a tumor or other selected location to form bubbles there and to release all or nearly all of any drug cargo there. Thus, this invention provides a way to increase concentrations of bubbles and drugs in a tumor or other selected location. This invention provides a way to achieve high concentrations of drugs having very short lifetimes in aqueous solutions. Moreover, it has been suggested that reducing tumor blood flow completely after agent had been delivered may provide therapeutic advantages. R. K Jain, "Delivery of novel therapeutic agents in tumors physiological barriers and strategies," Journal of the National Cancer Institute (NIH), 81, 570–576 (1989), page 575, incorporated by reference herein. The transient mechanical disruption of blood flow by bubble formation and vessel occlusion offers yet another advantage of this invention.

Ionizing radiation is useful to trigger the drops. The use of ionizing radiation as the triggering agent has several advantages. First, there is growing evidence than regimens combining concomitant radiation and drugs are more effective that regimens using sequential treatments. Preferred drugs for combined treatment with radiation are radiation sensitizers or bioreductive alkylating agents. Radiosensitizers such as misonidazole or etanidazole have proven effective in increasing the radiocurability of tumors in experimental animals. They have shown activity in several trials with human cancer patients, but the drug doses and number of drug treatments have been severely limited by toxicities which reflect the cumulative dose of drug delivered to certain normal tissues distant from the radiation field. The drug delivery system of this invention minimizes drug delivery to normal tissues with such treatment.

Bioreductive alkylating agents, such as mitomycin C and porfiromycin are selectively toxic to radiation-resistant hypoxic tumor cells; in animal systems these drugs produce supra-additive effects when given along with radiation. Clinical trials at Yale Medical School have shown that concomitant treatment with mitomycin C increases the cure of head and neck cancer over that seen with radiation alone. Trials with porfiromycin plus radiation in head and neck cancer and with mitomycin plus radiation in carcinoma of the cervix are ongoing. The drug dose and number of drug treatments is limited largely by the toxicity of the drug to marrow and by the possibility of toxicity to lung, kidney, and other tissues outside the radiation field. Better targeting of drug delivery by the system and method of this invention affords a way to reduce the toxic effects and to improve these regimens.

Delivery of drugs to a tumor by vaporizing superheated carrier drops using ionizing radiation also offers many technical advantages. Modern radiotherapy treatment planning techniques allow the delivery of radiation to the tumor volume with excellent precision, either through the use of multi-field external beam irradiation or through the use of brachytherapy (either low-dose-rate implants or high dose-rate remote afterloading).

Fluorocarbon carrier materials offer an additional advantage for combined chemotherapy and radiotherapy. These materials effectively transport oxygen, as well as drugs, to a tumor site which would otherwise be hypoxic, thereby increasing the tumor's radiosensitivity.

Modern ultrasound may also be used as triggering energy for bubble and drug delivery to selected regions. Superheated drops can be nucleated with sufficient intensities of short-pulse, low duty cycle (less than one percent) ultrasound, for example, with diagnostic ultrasound pulses (where the peak acoustic pressure exceeds approximately 1–3 MegaPascal, MPa) from a commercial scanner, for example, Advanced Technologies Laboratory's High Definition Imaging, HDI, system. In a test, superheated hexafluoropropylene drops were held in an aqueous host gel with a viscosity of a thin syrup and were triggered with ultrasound. Ultrasound was directed into the viscous liquid, whereupon bubbles were observed visually. In addition, it is known that acoustically-induced mechanical agitation of bubbles enhances diffusion, an advantage in distributing a delivered drug whether to nearby tumor or other targeted tissue. Moreover, the fact that drug-doped drops and triggered bubbles can be imaged by ultrasound is of value in non-invasively documenting drug distribution and in delineating tissue (e.g. tumor) structure.

Particular uses and advantages of dispersions and methods according to this invention in the treatment of disease and in the diagnostics associated with treatment, include:

a) local drug deposition;

b) capillary occlusion, (if the bubbles are triggered in small capillaries), which in some circumstances will aid in treatment by slowing the convection of drug away from the desired region, thereby giving the drug more time to diffuse and act in its therapeutic mode;

c) in-situ creation of contrast agents, because bubbles in vessels and capillaries are good contrast agents and, therefore, can be effectively imaged (e.g. with x-ray, ultrasound, or MRI);

d) superadditive effects of drugs and radiation by using therapeutic levels of radiation in conjunction with localized drug treatment;

e) oxygen delivery to hypoxic locations by use of an oxygen-carrying perfluorocarbon, thereby increasing the local susceptibility to radiation treatment of a tumor; and f) increasing drug diffusion by nucleating with ultrasound or radiation at a given location, and then agitating bubbles with ultrasound, the presence of an acoustic field at sufficient intensities and duty cycles and in an appropriate frequency range (e.g. from 20 kHz to 10 MHz) increasing drug diffusion into tissue by virtue of mechanical action of the sound field on the bubbles, thereby making drug treatment more efficacious.

EXAMPLE

The following dispersion is presently preferred for drug delivery. It is an emulsion, which means that the superheated drops can be concentrated without coalescing, as will be related. The described procedure for preparing it is a preferred method of preparation of a mechanically stable superheated drop drug delivery emulsion.

Drop material was a mixture. The major component of the drop material was chloro-pentafluoroethane ($C_2ClF_5$), which is superheatable. Another preferred material is hexafluoropropylene ($C_3F_6$). The drop material also contained acetone, in which the test drug mitomycin C was dissolved, and pentane. Both acetone and pentane are soluble in the halogenated ethane. Pentane was added to modify the boiling point and the density of the drops. Finally, one component of a surfactant combination was included, sorbitan monooleate (span 80).

The major component of the aqueous host solution was water or standard intravenous diluent. The host solution contained the coating material, such as bovine serum albumin (BSA), or a second component of a surfactant combination. With span 80, Tween 80 (poly oxyethylene sorbitan monooleate) was used. A minor amount of gelatin or other suspending agent may be added at this point, but the preferred procedure is to add it later, as will be described.

The function of each of the materials is summarized in the following table:

TABLE 1

| Material | Function |
|---|---|
| Chlorofluorocarbon | Volatile liquid component which permits drop composition to be superheated |
| Acetone | Dissolves the drug sample |
| Pentane | Adjusts degree of superheat of chlorofluorocarbon and drop density |
| Surfactant A (optional) | Aids drop formation when above 3 ingredients are mixed in aqueous phase |
| Drug material | Kills cancer cells |
| Aqueous phase or host | Diluent for carrying drug-carrying drops |
| Surfactant B | Works by itself or with Surfactant A to encapsulate drops |
| Suspending agent | Aids in uniformly suspending drops of doped drop material in aqueous phase |

Assembling these components into the final emulsion requires care. If not performed properly, the drops will not be mechanically stable and will boil prematurely. Mechanically stable compositions were made under pressure by adding the drop phase material to the aqueous phase through a two-way pressure-tight valve having fittings for syringe injection.

Two containers, denoted as A and B, were connected to one another through a pressure-tight valve. Acetone into which the test drug had been dissolved, pentane and chloropentafluoroethane ($C_2ClF_5$) were added to container A in nominal proportions 1:1:2. Container A was under the vapor pressure of the combined mixture, which I refer to as the "drop phase." Container A was cooled to maintain the vapor pressure under about 2–5 atmospheres (30–75 psi). When the combination of surfactant A and surfactant B was used to encapsulate the drops, surfactant A was also added to container A. (If BSA, also preferred, is used to encapsulate the drops, it is added to container B.) Acetone was chosen, because it dissolved the test drug and was soluble in the superheatable drop material. Selection of a dissolving agent appropriate for use with a particular superheatable material is a routine matter. It is noted that acetone is also miscible with the aqueous phase and is believed to bleed into that phase, causing at least some of the drug to precipitate out in the drops over time. As indicated earlier, the chosen drug may be soluble in the volatile component of the drop material, may be solubilized therewith, or may be added as a powder. Hence, acetone is optional. Pentane was added to adjust the degree of superheat of the chlorofluorocarbon: the more pentane added, the less the degree of superheat. Pentane also adjusted the density of the drops. It was added to minimize the degree of care required in assembling the components. The greater the degree of superheat, the greater the chance of premature vaporization, particularly when the drops are concentrated, which is a chain-reaction environment. Hence, pentane is optional. Pentane was soluble in the chlorofluorocarbon. Selection of a vapor pressure-adjusting material for a particular superheatable material is a routine matter.

The aqueous phase, which I refer to as the "host phase" was added to container B. In this case it was not the final aqueous phase for infusion. In addition to water or intravenous fluid, container B contained the encapsulant for the drops (for example, bovine serum albumin, BSA or one part of the encapsulant, here surfactant B). The materials in container B were maintained at slightly above 0° C.

The valve between containers A and B was opened. Due to the higher pressure of container A, its content flowed to container B, which was then sealed by closing the valve. Temperature of container B was maintained at about 0° C. The pressure in container B was the vapor pressure of the contents at that temperature.

The drop material was dispersed, in this case emulsified, in the host material in either of two ways: container B was shaken vigorously by hand, or container B was placed in an ultrasonic cleaner bath. Very small drops of drop material formed. The drops settled to the bottom, indicating that a stable emulsion was not formed. Drops did not coalesce, because they were protected by the encapsulant.

At this point, container B was opened. Despite a degree of superheat of about 15–30 Celsius degrees at this cold processing temperature, the drops did not vaporize upon decompression. The procedure to this point minimized the presence of nucleating gas pockets, so the drops were not triggered.

It was desired for this example that the emulsion be stable for a significant period, to permit storage for 2–3 months without the need to re-suspend the drops. Therefore, the drops were settled, and host liquid above the drops was carefully decanted. New host material was added, this time containing a small amount, less than one percent, of a carbomer to raise the viscosity to that of a light syrup, which greatly lowered the tendency to settle. Other compatible gelling agents, such as gelatin, can be substituted. The sealed container was gently shaken to suspend the drops throughout the aqueous phase.

A further optional stabilizing step may be used to reduce premature vaporization. The final emulsion is pressured to about 1000 psi for an hour or more to squeeze any undissolved gas in the material or on the container walls into solution. This was done by placing the final emulsion, held in container B, in a hydraulic pressure chamber, coupled to water in the chamber through a flexible plastic membrane (which replaced the cap on container B). After the pressurization step, the mixture in container B is returned to atmospheric pressure and re-sealed with a cap that holds pressure, and is stored in a refrigerator at about 4° C. until required for use.

Emulsification by simple agitation (shaking) will generally result in drops in the 10 to 100 $\mu$m diameter range. When using an ultrasonic generator (~21 KHz frequency), the drop size distribution is primarily in the 1–10 $\mu$m range. Using the sonicator technique, a sample was prepared in which 94% of the drops had diameters less than 10 $\mu$m. This corresponds to 70% of the total volume in drops that are smaller than 10 $\mu$m. We intend to make composition in which 95% of the drops will be below 5$\mu$m using the sonicator technique. As indicated earlier, bubbles have a diameter roughly six times that of the drops. Thus, bubbles formed by the method of this invention are not seen to be physically a problem to the body but rather to be removable naturally by the lungs, if not absorbed by the body.

Drug concentration in the drops can be measured by spectrophotometric techniques. Mitomycin C, the test drug, has a relevant absorbance peak at 360 nm. A typical test will be described. The test material was 0.4 ml superheated liquid (comprising 0.1 ml acetone solution of mitomycin C, 0.1 ml pentane and 0.2 ml $C_2ClF_5$) introduced into a water solution of Bovine Serum Albumin (BSA), which is one of the test encapsulant materials that has been tested. Drops were generated by sonicating this mixture. After the drug-bearing drops precipitated to the bottom of the container, the residual aqueous solution was removed and 10 ml distilled water was added. Then all drops were triggered to boil by heating them to over 60° C., which is above the homogeneous nucleation temperature of drops of this composition, but which is not high enough to decompose the mitomycin.

Optical absorption of the final water-plus-released drug was performed with a Beckman, model DU-2 spectrophotometer. Used as reference liquid was an aqueous solution of mitomycin C with a concentration of 1 $\mu$M. It was determined that the concentration of mitomycin C in the test liquid was 12 $\mu$M. Based on the known ratio of drop material to added water, we thus determined that the concentration of drug in the drops themselves was approximately 300 $\mu$M. These measurements were preliminary and accurate to ±25%.

Tests performed with drops not containing any drug were also performed and gave optical absorption equivalent to that observed for the control, water.

The bubble production rate for a given dispersion of drops is evaluated simply by exposing a known amount of drop material to a source whose radiation flux is known at the position of the sample, and just counting acoustically the number of bubble "popping" events that occur per unit time. A typical test will now be described.

This test employed a 56.7 millicurie (mCi) Cesium 137 gamma source. The contents of container B consist of 0.4 ml of the drops phase and 9.6 ml of the aqueous phase. The drops phase contained 0.1 ml acetone, 0.1 ml pentane and 0.2 ml $C_2ClF_5$. The aqueous phase contained water, carbomer gelling agent (Carbopol® 1342 from B.F. Goodrich) and BSA emulsifier. In order to reduce radiation sensitivity, 0.3 ml of the emulsion was taken and diluted in 5 ml of additional diluent. It was tested by acoustically counting the number of bubble events. The result was a sensitivity of 27 (accurate to ±15%) counts per millirad per mg of drop material. Therefore, for a 100 rad irradiation (1 Gy), which would be high for diagnostic uses but low for therapeutic effects, a count of roughly 2.7 million bubbles formed per mg of drop material (which does not include the aqueous diluent) would be expected. At the drug concentration in the test drops of 300 $\mu$M, a dose of 1 $\mu$g of drug (molecular weight 334) would be carried by 10 mg of drop material. As a rough calculation, if all drops were 7 $\mu$m in diameter (the approximate center of the measured distribution), then there would be 5.8 million drops in one mg of drop material. Thus, 1 Gy of radiation appears to result in the vaporization of approximately half of the drops in the sample. (This order-of-magnitude calculation ignores depletion effects.)

Ultrasound negative pressure (during the rarefaction part of the sound wave) is equivalent to the superheat caused by elevated temperature. The peak negative pressures of many diagnostic ultrasound machines can exceed 3 MPa (30 atmospheres). The usefulness of ultrasound as a nucleating agent was tested by pouring drop-bearing composition into a water bath at 37° C., through the focal zone of a 2.5 MHz ultrasound transducer from a Hewlett Packard SONOS 100 ultrasound scanner. The drops in the composition, which had a density slightly greater than water, fell in the bath, whereas the triggered bubbles, which were buoyant, rose, making an assessment of ultrasound effectiveness straightforward. If the ultrasound is effective, one sees small bubbles rising in the bath. As a control, the ultrasound was turned off and the focal zone was observed with an optical cathetometer to see if bubbles formed. The SONOS scanner was turned on and the results observed.

At an output intensity of approximately 100 Watts/cm$^2$ (spatial peak, pulse average), or greater, bubbles were nucleated, whereas in the control with sound off, no bubbles were generated. One can make an estimate of the peak negative pressure, assuming an acoustic plane wave in the focal zone. In this way, the peak negative pressure was estimated to be 1.7 MPa (17 atmospheres). This, of course, is a maximum estimate. An NTR miniature immersible hydrophone was also used. With it we measured a nucleation threshold of 4–5 atmospheres peak negative pressure. These measurements confirmed that diagnostic pulses with duty cycles less than one percent can trigger drops to release their drug cargo.

Before the initiation of tests using biological cell cultures or experimental animals, procedures were developed to ensure the sterility of the drop composition samples. Since the procedures used in processing the composition required certain steps that would prevent standard sterilization techniques (gas sterilization or autoclaving) sterilization procedures which relied on exposure of pressurized samples (i.e. ones that are without superheat and therefore not sensitive to radiation) to gamma rays (45 Gy) from a Cs-137 source or exposure of the samples to intense ultraviolet irradiation were tested. Irradiation procedures were found, both with UV and with gamma irradiation, to result in complete sterilization of approximately half of the samples. The sterility of the cultures was tested using standard clinical sterility tests and a variety of nutrient media and agars, with up to two weeks of incubation. Higher irradiations levels are believed to produce 100% bacteria-free samples.

The effects of the drops on mammalian cells were examined using EMT6 mouse breast carcinoma cells, using techniques for studies examining the effects of radiation, radiosensitizers, and a wide variety of chemotherapeutic drugs. EMT6 cells were grown as monolayer cultures attached to the growth surfaces of cell culture dishes and overlaid by a liquid nutrient medium (Waymouth's medium supplemented with 15% serum). All studies were performed using exponentially growing monolayers. The sterile emulsion (~20 to 50 $\mu$l total amount) was gently pipetted onto the top of the medium, and drops were distributed uniformly over the cultures by gentle swirling of the dishes. The drops, which were denser than the growth medium, fell to rest on the surface of the cells and the dish. Preliminary studies included: a) untreated control cultures, b) cultures to which drops were added, but no radiation was given to trigger bubble formation, c) cultures treated with both the drop composition and radiation (1 Gy of x-rays from a 250 kV x-ray source, delivered 5 min after the addition of the drops to trigger boiling), and d) cultures receiving radiation alone. For the amounts of dispersion tested (20–50 $\mu$l), neither the intact drops nor the drops without drug triggered to lysis by x-rays altered in a significant way either the number of intact cells in the cultures or the viability of the cells, as tested by suspending the cells after treatment and assaying their ability to form colonies. These experiments showed that the intact drops were not toxic to tumor cells during the 1 hr. incubation. Moreover, neither the process of triggering the drops into bubbles near the tumor cells nor the materials released by the drops after lysis were toxic to these cells at the concentrations used in these experiments.

In subsequent studies, compositions were prepared analogously, but the antineoplastic drug mitomycin C was incorporated into the drops. Mitomycin C is a bioreductive alkylating agent which is widely used in the treatment of solid tumors. Preliminary studies were performed to examine the effects of drops containing mitomycin C. These experiments included a) untreated controls, b) unlysed drops, containing no drug, c) radiation-triggered drops, containing no drug, and d) radiation alone. In addition, groups treated with e) untriggered drug-containing drops, f) radiation-triggered, drug-containing drops, and g) free mitomycin C ("MC"), were included:

TABLE 2

Survival Fraction - Cell Culture Tests

| Treatment | Surviving Fraction |
| --- | --- |
| a. Untreated controls | 1.00 |
| b. Unlysed drops, no drug | 1.03 |
| c. Radiation-triggered drops, no drug | 0.94 |
| d. Radiation alone | 0.85 |
| e. Unlysed drops containing MC | 0.77 |
| f. Radiation-triggered drops containing MC | 0.49 |
| g. 2 $\mu$M MC (drug control) | 0.017 |

Geometric mean of Surviving Fractions were determined in two independent experiments. Because 2 samples were tested in groups e. and f. in each of these experiments, these means are for a total of four samples.

Formulations of the drug-bearing drops were found to contain up to 300 $\mu$M mitomycin. Drops were dispersed in an aqueous diluent at a volume fraction of 0.04, so that the effective concentration in the suspension was 12 $\mu$M. Five drops of suspension pipetted onto the cell culture have a volume of approximately 50 $\mu$l. Therefore, the maximum total concentration of drug deposited on the cell culture, after irradiation, would be 0.12 $\mu$M if all of the drops were triggered and 0.06 $\mu$M if 50% of the droplets were triggered to bubble formation, as measured in the dose-bubble formation studies described above. This amount can be compared to the concentration of free mitomycin C used in one of the controls of 2.0 $\mu$M, the range used in reported studies of the biological effects of this drug. Based on those studies of the survival of EMT6 cells treated with different doses of mitomycin C, it was estimated that a 1 hr. treatment with 0.12 $\mu$M mitomycin C should result in a surviving fraction of approximately 0.8. These predicted survival fractions are in fair agreement with that observed in the experiments, shown in Table 2, given the uncertainties involved in testing these preliminary formulations, and taking into account that the radiation given to the cells has a moderate toxicity by itself.

The tests reported above indicate that superheated drops can be doped with drugs and encapsulated in an aqueous diluent, and that these drops can be triggered by x-ray irradiation at levels significantly lower than therapeutic regimens of radiation (and also by diagnostic levels of ultrasound), thereby releasing their cargo of drugs.

Although the amount of drug released in cell culture tests was only 3% of the control with drugs directly used on the cell culture in one test and about 6% in a second test, there was a measurable decrease in the growth of EMT6 cells. When drops not containing drugs were triggered to boil, no similar decrease in cell activity was observed. It was found that much greater amounts of drops material tested caused EMT6 cells to react negatively, becoming unplanted from the petri dish. Some component, perhaps in the particular encapsulant, had a toxic effect on the cells at high concentrations. Since a number of different encapsulants can be used in this invention or encapsulants can be omitted entirely, this side effect is not inevitable.

Our work indicates the drop material can be triggered in great enough proportions with amounts of x-rays significantly lower than therapeutic doses. We found that 1 $\mu$g of drug carried in approximately 10 mg of drop material (carried in 0.25 ml of normal suspension) could be infused in 2.5 minutes at a rate of 0.1 ml per minute. If exposed to 1 Gy of x-rays at the position of a tumor, over 2 million bubbles, or approximately one half of the drops, would be triggered, releasing drug into the tumor. These results imply that a bearable radiation exposure to the patient will release adequate amounts of chemotherapeutic drug into a tumor, releasing significantly less drug outside the tumor region, thereby sparing normal tissue and allowing for a spatial partitioning.

The above examples are given for the purpose of illustration, not as a limitation. Other useful embodiments containing no drugs or different drugs and other materials, and different proportions of materials, are included in this invention and are within the skill of the art.

I claim:

1. A dispersion for therapeutic or diagnostic use comprising an aqueous continuous phase suitable for infusion into a human or other animal and dispersed drops comprising a practically immiscible superheated liquid, said drops having an average diameter of 0.05–20 $\mu$m, being physically stable in said composition and in said body and having an amount of superheat of at least 17 Celsius degrees, said amount of superheat being sufficient to permit their in-body nucleation by a level of ionizing radiation or ultrasound tolerable to said body.

2. The dispersion according to claim 1 wherein said superheated liquid comprises at least one component selected from the group consisting of fluorocarbons, chlorofluorocarbons, hydrocarbons and mixtures thereof.

3. The dispersion according to claim 1 wherein said superheated liquid has a boiling point at atmospheric pressure below −15° C.

4. The dispersion according to claim 1 further comprising a gelling or thickening agent.

5. The dispersion according to claim 1 wherein said drops further comprise at least one drug that is releasable by nucleation of said drops.

6. The dispersion according to claim 5 wherein said superheated liquid has a boiling point at atmospheric pressure below −15° C.

7. The dispersion according to claim 6 further comprising an emulsifier.

8. The dispersion according to claim 6 wherein said superheated liquid comprises at least one component selected from the group consisting of fluorocarbons, chlorofluorocarbons, hydrocarbons and mixtures thereof.

9. The dispersion according to claim 5 wherein said superheated liquid includes a solvent for said at least one drug.

10. The dispersion according to claim 9 further comprising an emulsifier.

11. The dispersion according to claim 5 wherein said at least one drug is selected from the group consisting of radiation sensitizers and bioreductive alkylating agents.

12. The dispersion according to claim 1 wherein said aqueous phase comprises an intravenous solution.

13. The dispersion according to claim 1 further comprising an emulsifier.

14. A method of delivering at least one drug to a selected body location comprising the steps of:
   a) infusing a dispersion according to claim 5; and
   b) selectively subjecting said body location to energy from the group consisting of ionizing radiation and ultrasound to vaporize the drops of said dispersion, thereby releasing said drug at said body location.

15. The method according to claim 14, wherein said energy is ionizing radiation.

16. The method according to claim 15, wherein said energy is produced by a radiation source implanted in said body at or near said selected body location.

17. The method according to claim 14 wherein said dispersion contains an emulsifier.

18. The method according to claim 14 wherein the superheated liquid in said dispersion has a boiling point at atmospheric pressure below −15° C.

19. The method according to claim 14 wherein said step of infusing comprises injecting intravenously.

20. The method according to claim 19 wherein said energy is ionizing radiation.

21. The method according to claim 19 wherein said superheated liquid comprises at least one component selected from the group consisting of fluorocarbons, chlorofluorocarbons, hydrocarbons and mixtures thereof.

22. The method according to claim 14 wherein said dispersion is an emulsion, wherein said superheated liquid comprises at least one component selected from the group consisting of fluorocarbons, chlorofluorocarbons, hydrocarbons and mixtures thereof, and wherein said superheated liquid has a boiling point at atmospheric pressure in the range of below −15° C.

23. The method according to claim 22 wherein said superheated liquid includes a solvent for said at least one drug.

24. The method according to claim 14 further comprising the step of stimulating vaporized drops with ultrasound to impart motion thereto sufficient to increase diffusion of said at least one drug.

25. The method according to claim 14, further comprising the step of monitoring said infusion and vaporization by diagnostic imaging of said selected body location using bubbles formed by said vaporization as contrast agents.

26. In the process of diagnostically imaging a selected body location, the improvement comprising injecting intravenously a dispersion according to claim 1 and subjecting said body location to ionizing radiation or ultrasound to vaporize the drops of said dispersion, thereby producing at said location bubbles which serve as contrast agents.

27. The method according to claim 14, wherein said at least one drug is selected from the group consisting of radiation sensitizers and bioreductive alkylating agents.

28. A method of delivering gaseous bubbles to a selected body location comprising the steps of infusing a dispersion according to claim 1 and selectively subjecting said body location to energy selected from the group consisting of ionizing radiation and ultrasound to vaporize the drops of said dispersion.

29. The method according to claim 28 wherein said step of infusing comprises intravenous injection, wherein said selected body location includes capillaries, and wherein vaporization of said drops occludes said capillaries.

30. The method according to claim 29 wherein said dispersion includes an emulsifier.

31. The method according to claim 28 wherein a drug is delivered to said selected body location, further comprising the step of stimulating vaporized drops with ultrasound to impart motion thereto sufficient to increase diffusion of said drug.

\* \* \* \* \*